United States Patent [19]

Warner

[11] 4,030,485

[45] June 21, 1977

[54] METHOD AND APPARATUS FOR CONTINUOUSLY MONITORING SYSTOLIC BLOOD PRESSURE

[76] Inventor: Glenfield Warner, 3010 Matis St., Ville St. Laurent, Quebec, Canada, H4R 1A3

[22] Filed: Nov. 12, 1974

[21] Appl. No.: 523,196

[52] U.S. Cl. .......................... 128/2.05 A; 128/2 L; 128/2.05 M
[51] Int. Cl.² ........................................ A61B 5/02
[58] Field of Search ............... 128/2.05 A, 2.05 M, 128/2.05 N, 2.05 P, 2.05 Q, 2.05 R, 2 L

[56] References Cited
UNITED STATES PATENTS

| | | | |
|---|---|---|---|
| 2,827,040 | 3/1958 | Gilford | 128/2.05 A |
| 3,628,525 | 12/1971 | Polanyi | 128/2.05 P |
| 3,633,568 | 1/1972 | Hobel | 128/2.05 M |
| 3,776,221 | 12/1973 | McIntyre | 128/2.05 R |
| 3,841,314 | 10/1974 | Page | 128/2 L |
| 3,850,169 | 11/1974 | Gebben et al. | 128/2.05 A |
| 3,903,872 | 9/1975 | Link | 128/2.05 A |

OTHER PUBLICATIONS

George et al., "Measurement of Max . . . Pressure in Man", Med. Res. Eng., 4th Qt., 1967, pp. 21–24.

Naylor, "Analog Preprocessor . . . pressure", Bio-Med. Eng., vol. 6, No. 2, Feb. 1971, pp. 77–80.

Primary Examiner—Robert W. Michell
Assistant Examiner—Lee S. Cohen
Attorney, Agent, or Firm—Alan Swabey & Co.

[57] ABSTRACT

The invention relates to a method and apparatus for continuously monitoring systolic blood pressure of a subject. The instrument includes a light transducer for detecting variations in light intensity corresponding to variations in blood volume of tissue of the subject under the transducer and for converting the changes in light intensity to changes in voltage. In one embodiment, a heater is provided to dilate the tissue under the transducer. The voltage signals are differentiated with respect to time, and the differentiated signal is sampled once every heart beat of the subject at the beginning of diastole, or at the maximum value of the differentiated signal sampled during diastole, to produce a sampled voltage signal. To this sampled voltage signal is added a voltage representative of a steady pressure, and the sum is a voltage representative of systolic pressure. The amplitude of the steady pressure is a function of blood pressure in the aorta and large arteries of the subject, stiffness of the aorta and large arteries, and the total peripheral resistance of the subject.

18 Claims, 16 Drawing Figures

TABLE 1

Measurements of the Pulse and Alpha Waves in Patients with Renal Hypertension [35]

| SUB-JECT NO. | AGE | SEX | BLOOD PRESSURE | PART | VOLUME OF PART STUDIED | VOLUME OF THE DEFLECTIONS OF THE ALPHA WAVES | | FREQUENCY OF THE DEFLECTIONS OF THE ALPHA WAVES | | | VOLUME OF THE PULSE WAVES | | |
|---|---|---|---|---|---|---|---|---|---|---|---|---|---|
| | | | | | | MEAN | MAXI-MUM | MEAN | MAXI-MUM | MINI-MUM | MEAN | MAXI-MUM | MINI-MUM |
| | years | | mm. Hg | | cc. | cu.mm./5 cc. of part | | No. per minute | | | cu.mm./5 cc. of part | | |
| 39 | 46 | M | 200/120 | F* | 4.2 | 14.0 | 38.2 | 7.8 | 10 | 5 | 12.5 | 15.0 | 7.7 |
| | | | | T* | 4.0 | 7.1 | 22.2 | 11.0 | 13 | 10 | 5.2 | 6.2 | 4.5 |
| | | | | P* | 2.0 | 5.2 | 17.3 | 10.0 | 17 | 7 | 9.5 | 9.7 | 9.0 |
| 40 | 38 | F | 220/148 | F | 3.9 | 19.8 | 54.5 | 11.6 | 12 | 6 | 6.8 | 7.6 | 6.4 |
| | | | | T | 3.1 | 5.1 | 36.9 | 11.2 | 12 | 5 | 2.9 | 3.0 | 2.9 |
| | | | | P | 1.2 | 4.5 | 20.0 | 9.8 | 15 | 6 | 1.6 | 1.6 | 0.8 |
| 44 | 42 | M | 198/140 | F | 7.1 | 12.3 | 37.3 | 8.0 | 9 | 6 | 4.0 | 4.6 | 3.5 |
| | | | | T | 6.1 | 5.2 | 13.8 | 8.4 | 10 | 5 | 2.1 | 2.4 | 1.1 |
| | | | | P | 3.0 | 4.1 | 10.1 | 10.2 | 14 | 7 | 8.4 | 10.0 | 0.5 |
| 57 | 40 | F | 190/138 | F | 3.2 | 12.4 | 47.4 | 7.8 | 10 | 6 | 5.7 | 7.0 | 4.7 |
| 72 | 27 | F | 200/140 | F | 3.2 | 14.3 | 50.8 | 14.2 | 18 | 12 | 9.1 | 10.2 | 6.9 |
| | | | | T | 3.9 | 5.4 | 19.5 | 10.2 | 13 | 7 | 2.7 | 3.9 | 2.5 |
| 74 | 28 | F | 184/124 | F | 3.5 | 11.1 | 38.2 | 9.8 | 10 | 9 | 3.3 | 5.6 | 2.2 |
| | | | | T | 3.3 | 7.7 | 23.0 | 11.2 | 14 | 10 | 8.3 | 9.7 | 6.8 |
| Mean, maximum and minimum for the group | | | | F | | 14.0 | 54.5 | 9.9 | 18 | 5 | 8.2 | 15.0 | 2.2 |
| | | | | T | | 5.1 | 36.9 | 10.4 | 13 | 5 | 4.2 | 9.7 | 1.1 |
| | | | | P | | 4.6 | 20.0 | 10.0 | 17 | 6 | 6.5 | 10.0 | 0.5 |

*F = Right index finger tip.
T = Right second toe tip.
P = Postero-superior portion of the right pinna.

Fig. 3

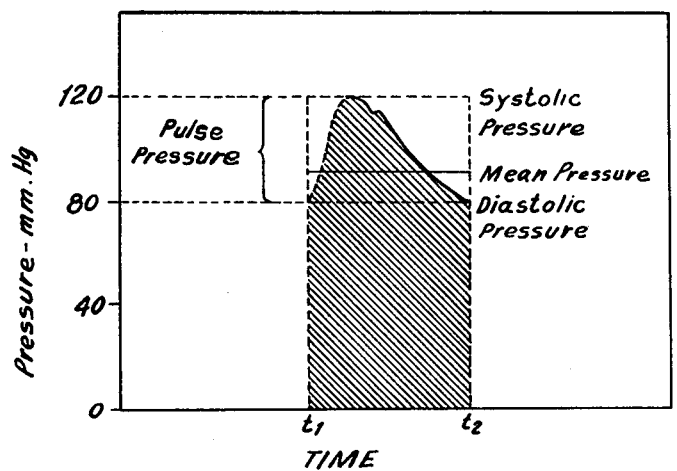
Fig. 4.1
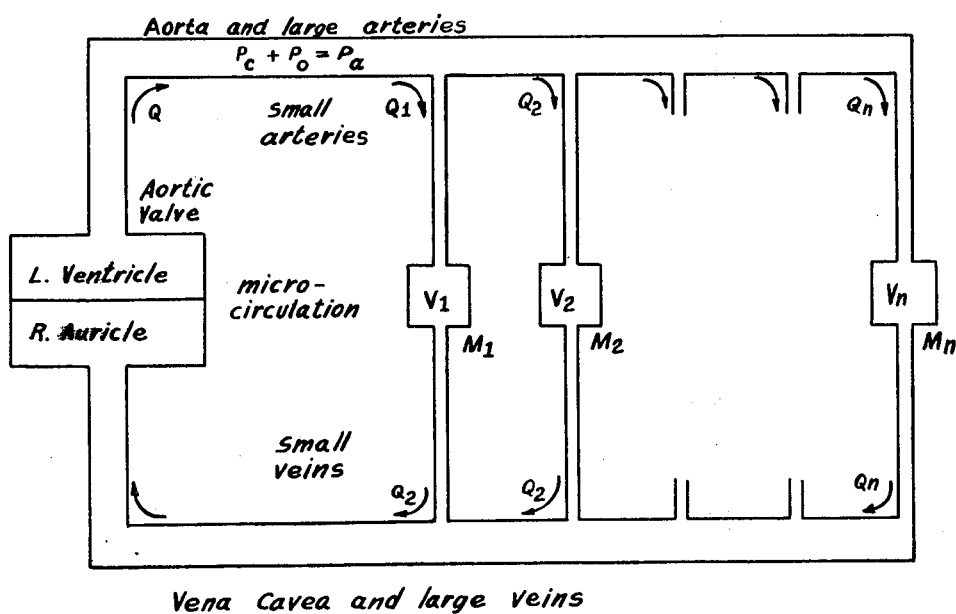
Fig. 4.2

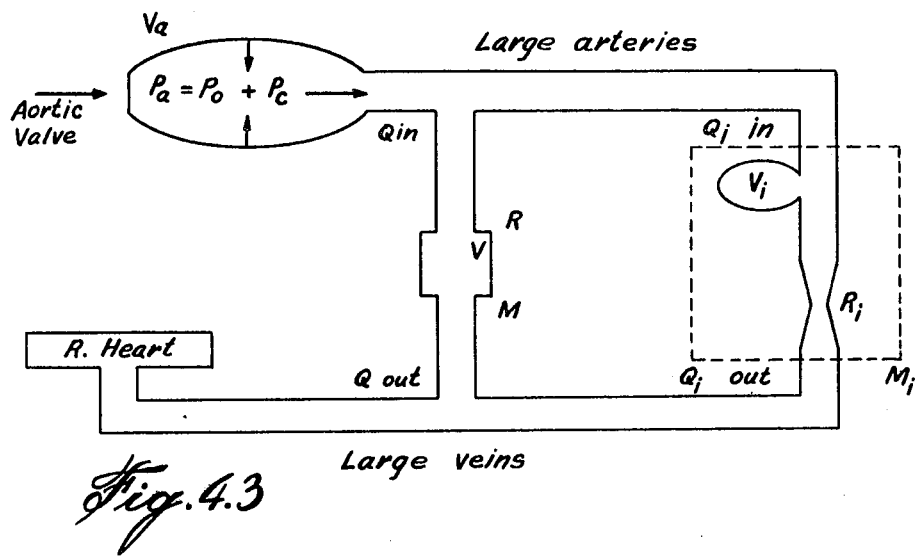
Fig. 4.3
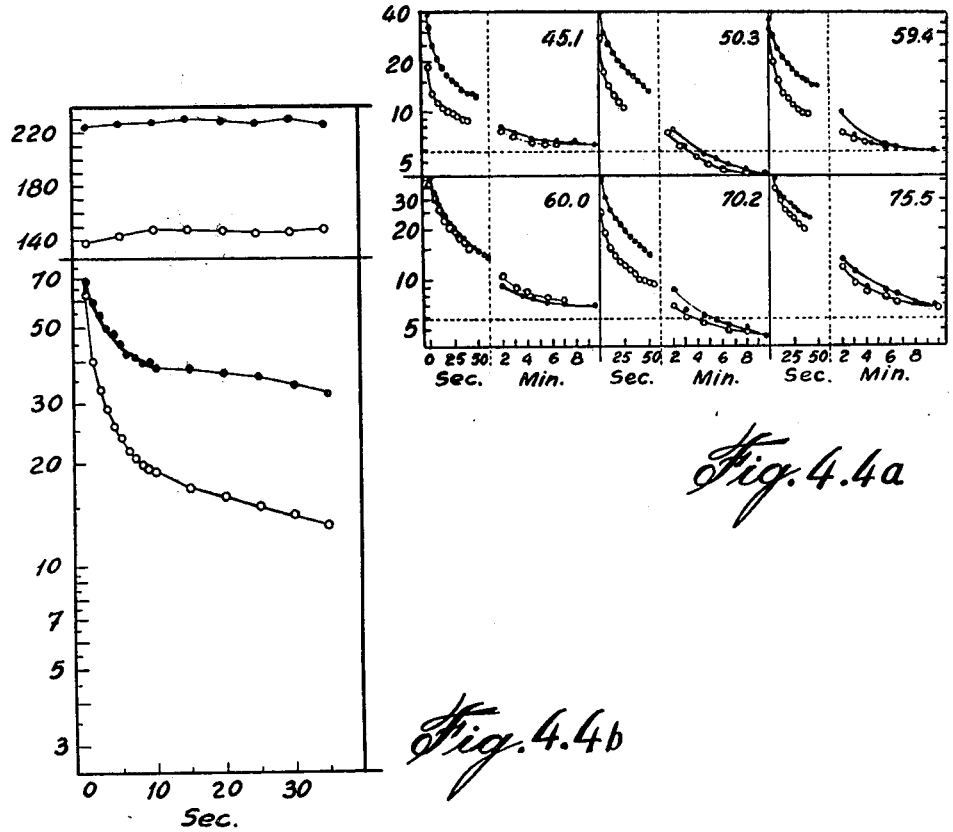
Fig. 4.4a
Fig. 4.4b

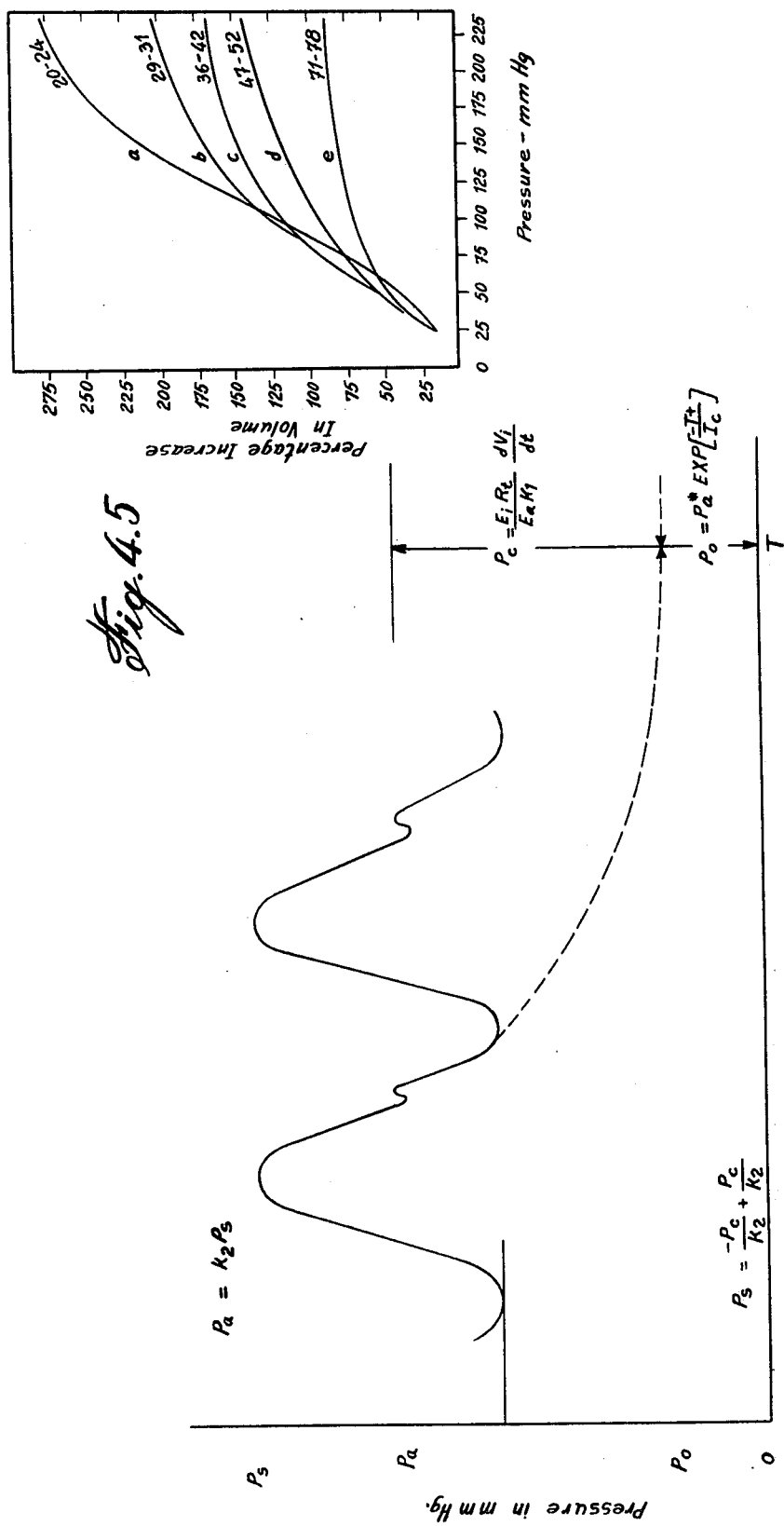

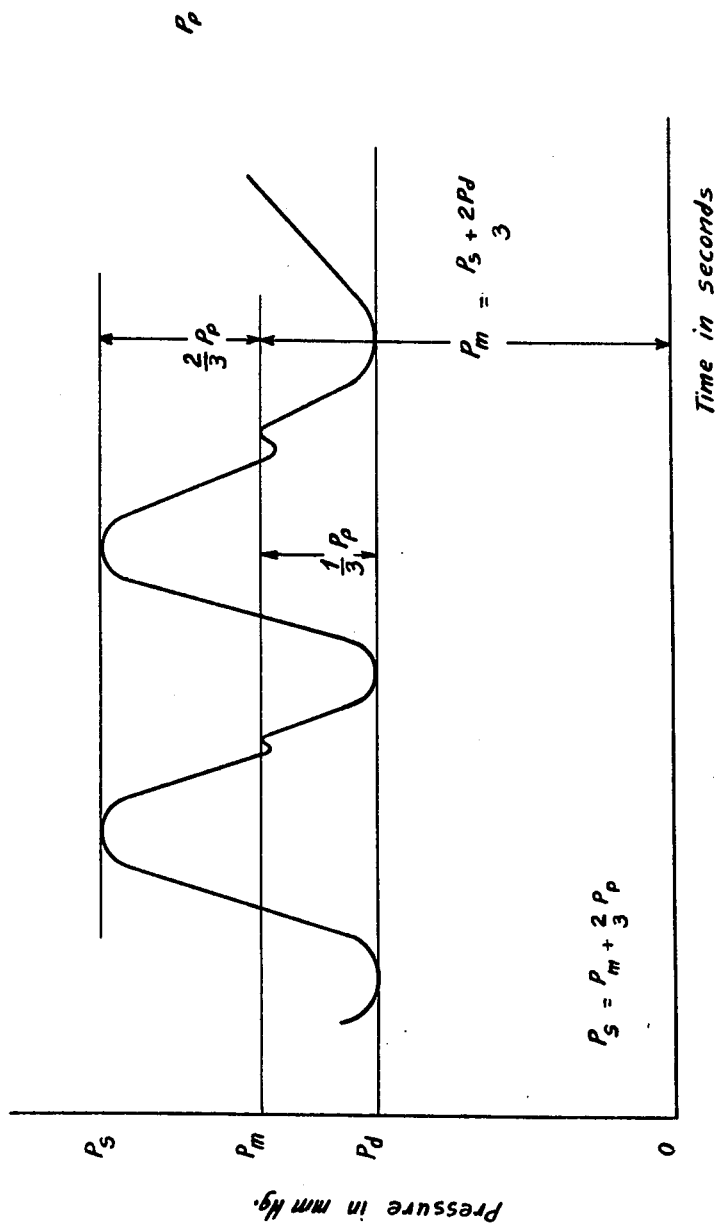
Fig. 4.6b

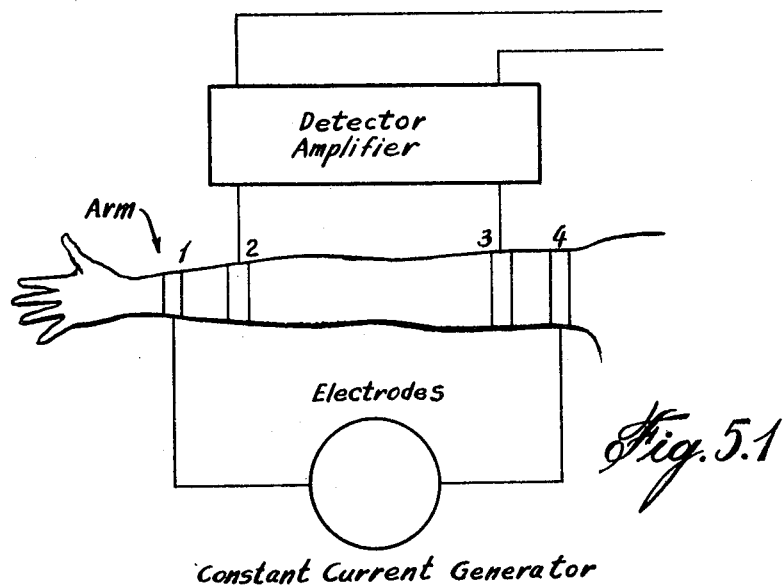
Fig. 5.1
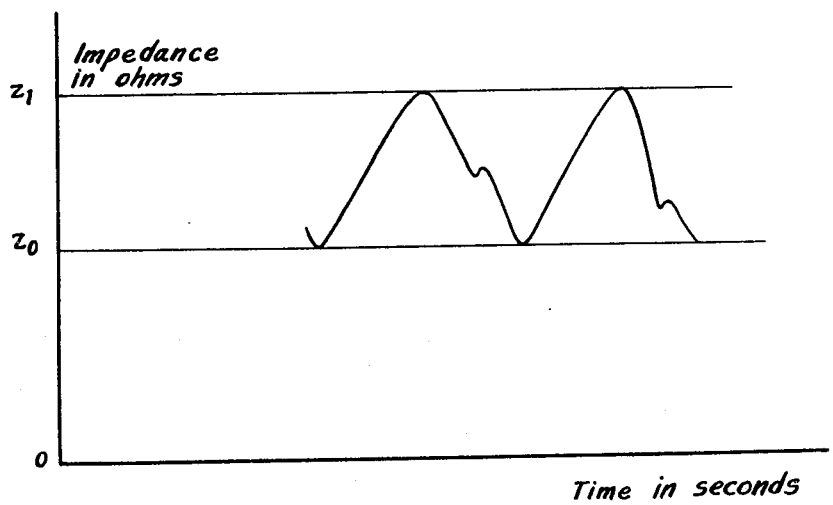
Fig. 5.2

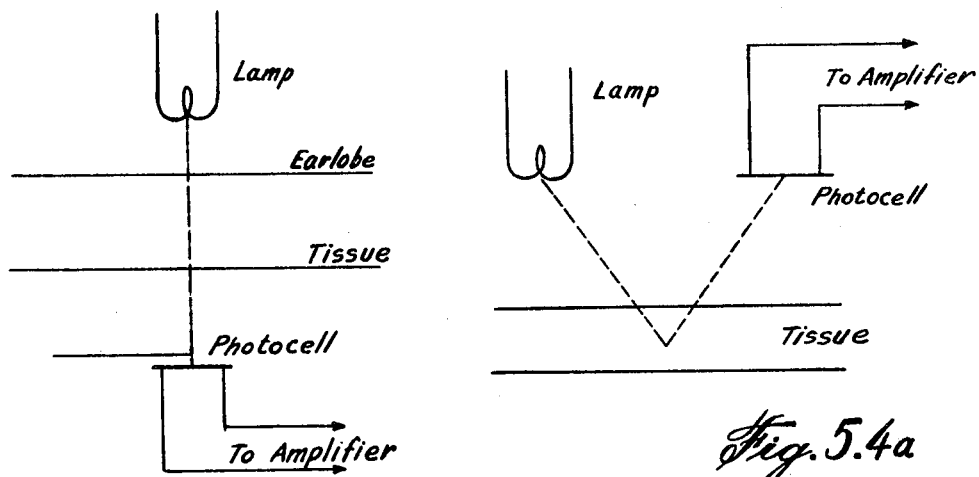
Fig. 5.3a
Fig. 5.4a
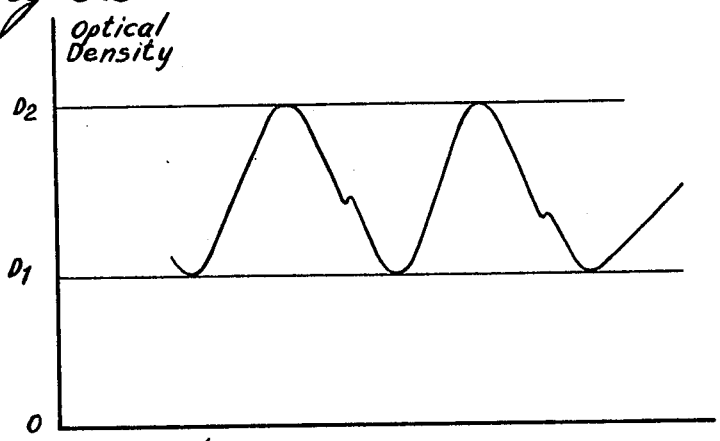
Fig. 5.3b
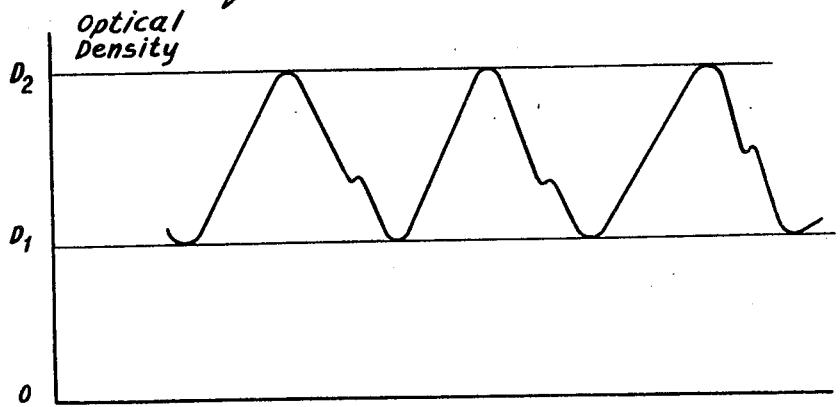
Fig. 5.4b

METHOD AND APPARATUS FOR CONTINUOUSLY MONITORING SYSTOLIC BLOOD PRESSURE

BACKGROUND OF THE INVENTION

1. Field of the Invention

The invention relates to a method and apparatus for continuously monitoring the blood pressure of patients under hospital, or other conditions. More specifically, the invention relates to such a method and apparatus for continuously monitoring systolic blood pressure by detecting variables proportional to blood pressure.

2. Description of the Prior Art

An interesting and informative survey of methods for measuring blood pressure is given in a book by L. A. Geddes published by the *Yearbook Medical Publishers, Inc.*, Chicago, 1970, entitled "The Direct and Indirect Measurement Of Blood Pressure". The method include direct method with a transducer outside the artery, as discussed by T. E. Piemme in his article in *Progress In Cardiovascular Diseases*, 5, (1963), p. 574 in an article entitled "Pressure Measurements: Electrical Pressure Transducer"; a direct method with the transducer inside the artery, which is discussed by H. P. Pieper in the *Journal of Applied Physiology*, 22, February 1967, in an article entitled "Catheter Tip Manometer for Measuring Blood Pressure During Changes"; and the well known indirect occlusive method wherein an inflatable cuff is wrapped around the arm. The last mentioned method is commonly used by doctors in their offices as well as during examinations in the hospital.

The first two methods require the puncturing of an arterty, and the last method cannot be used for continuously monitoring blood pressure over long periods of time as the cuff must be inflated each time a reading is to be taken.

SUMMARY OF THE INVENTION

It is an object of the invention to provide a method and apparatus which can be used under hospital and other conditions.

It is a further object of the invention to provide such a method and apparatus which will permit the continuous monitoring of blood pressure.

It is a more specific object of the invention to permit the continuous monitoring of systolic blood pressure.

In accordance with the invention, a method for continuously monitoring systolic pressure in a human or animal subject by means of a calibrated instrument including light transducer means for converting variations in light intensity to variations in amplitude of an electrical quantity comprises;

detecting, with said transducer, variations in light intensity corresponding to variations in blood volume of the tissue of the subject under the transducer;

whereby the output of said transducer comprises variations in amplitude of said electrical quantity corresponding to said variations in blood volume;

differentiating said variations in amplitude of said electrical quantity with respect to time to provide a differentiated amplitude representative of the rate of said variations in blood volume;

periodically selecting a sample of said differentiated amplitude; and adding to said sample an amplitude of a like electrical quantity representative of a steady pressure;

to thereby produce an electrical signal whose amplitude is proportional to systolic pressure of said subject.

Preferably, the samples are selected once every heart beat of the subject at the begining of diastole, or at the maximum value of the differentiated signal during diastole.

The amplitude of the steady pressure is a function of blood pressure in the aorta and large arteries of the subject, stiffness of the aorta and large arteries and total peripheral resistance of the blood of the subject.

Preferably, the tissue under the transducer is dilated by means of a heater.

Further, in accordance with the invention, a calibrated instrument for continuously monitoring the systolic pressure of a human or animal subject including a display meter and a transducer detecting variations in light intensity corresponding to variations in blood volume of said subject in the area of said transducer and for converting said variations in light intensity to variations in amplitude of an electrical quantity; comprises;

differentiating means for differentiating said variations in amplitude of said electrical quantity with respect to time to provide a differentiated amplitude representative of the rate of said variations in blood volume;

sampling means for periodically selecting a sample of said differentiated amplitude;

means for providing an amplitude of a like electrical quantity representative of a steady pressure;

adding means to add said sample and said amplitude representative of steady pressure;

whereby to produce an electrical signal whose amplitude is proportional to the systolic pressure of said subject to drive said meter.

In a preferred embodiment, heating means are provided to dilate the tissue under the transducer.

BRIEF DESCRIPTION OF THE DRAWINGS

The invention will be better understood by an examination of the following description together with the accompanying drawings in which.

BRIEF DESCRIPTION OF THE DRAWINGS IN THE APPENDIXES

Theory and measuring techniques are described in the appendixes together with the drawings referred to therein in which:

FIG. 3 is Table I showing measurements of pulse and alpha waves in patients with renal hypertension;

FIG. 4.1 is a graph of pressure against time showing arterial systolic, diastolic, diastolic, pulse and mean pressures;

FIG. 4.2 is a schematic representation of microcirculation during diastole;

FIG. 4.3 is a schematic representation of lumped circulation during diastole;

FIG. 4.4a is a graph of pressure against time showing the fall of pressure in an occluded dog artery;

FIG. 4.4b is a graph of pressure against time showing the fall of pressure in an occluded dog artery before and after vasoconstriction;

FIG. 4.5 is a graph of percentage increase in volume against pressure showing the percentage change in volume of an aorta with an increase in pressure;

FIG. 4.6a is a graph of pressure against time showing the relationship between $P_s$, $P_c$, $P_a$ and $P_o$;

FIG. 4.6b is a graph of pressure against time showing the relationship between $P_s$, $P_d$, $P_m$ and $P_p$;

FIG. 5.1 is a schematic diagram of electrical impedance plethysmograph;

FIG. 5.2 is a graph of impedance against time showing waveform of impedance variations;

FIG. 5.3a is a schematic diagram of an absorption type photoelectric plethysmograph;

FIG. 5.3b is a graph of optical density against time showing the waveform of optical density variations;

FIG. 5.4a is a schematic diagram of a reflectance type photoelectric plethysmograph; and FIG. 5.4b is a graph of optical density against time showing the waveform of optical density variations.

DESCRIPTION OF THE PREFERRED EMBODIMENTS

Appendix "A", attached hereto, discusses the theory behind the inventive apparatus and method while Appendix "B" describes measuring techniques known in the art. Equation 5.1 in Appendix B reads:

$$P_s = \frac{P_a}{K_2} \mathrm{EXP}\left[-\frac{E_a}{R_t}T^+\right] + \frac{E_1 R_t}{E_a K_1 K_2} \frac{dV_t}{dt}$$

In this equation, there are two variables to be measured, to wit, $$\frac{dV_t}{dt} \text{ and } T_c \left(=\frac{R_t}{E_a}\right).$$

As was mentioned in the summary to Appendix B, under easily implementable conditions, $T_c$ can be taken as a constant. Under these conditions, the above equation is reduced to:

$$P_s = P_2 + K_5 \frac{dV_t}{dt}$$

where
$P_2$ = a steady pressure
$K_5$ = constant.

As mentioned in the Appendices, and as can be seen in the first formula above, the steady pressure is a function of blood pressure in the aorta and large arteries of the subject, stiffness of the aorta and large arteries, and total peripheral resistance of the blood of the subject.

Figure 1:
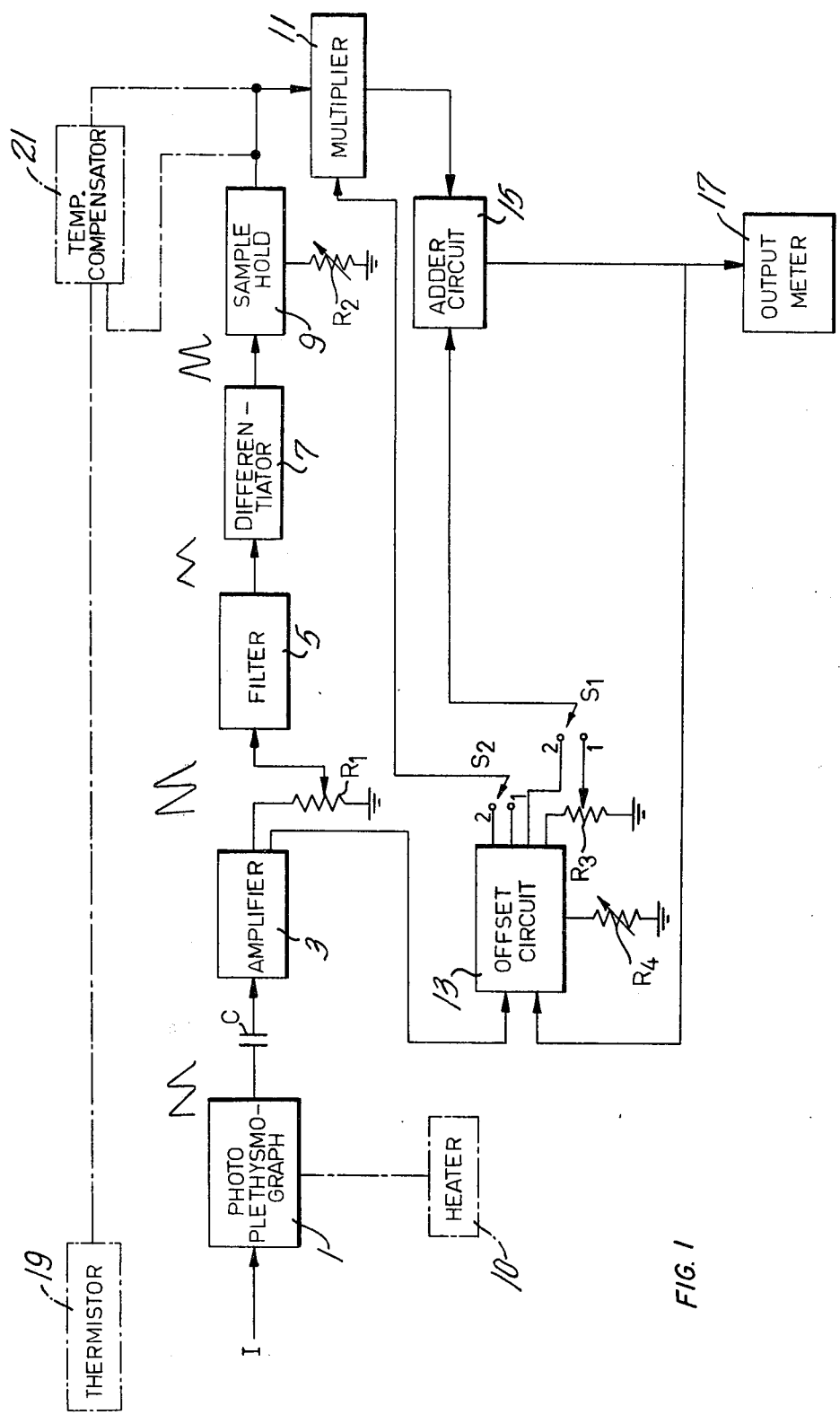
FIG. 1 is a generalized block diagram of the inventive apparatus for carrying out the method in accordance with the invention.

FIG. 1 shows an instrument which can be used to monitor blood pressure when $T_c$ is taken either as a constant or as a variable.

Referring to FIG. 1, the instrument includes light from a light source is applied to photo plethysmograph 1 either by transmission through the skin or by reflectance from the skin as discussed in Appendix B. As mentioned in Appendix B, the plethymograph comprises a light transducer which detects variations in light intensity corresponding to variations in blood volume of a subject in the area of the transducer ($V_t$ in the above formulae), and converts these variations to variations in the amplitude of an electrical quantity — preferably voltage. The output of 1 is fed to amplifier 3 through a capacitor C to remove the DC or reference level. In amplifier 3, the few millivolts at the output of 1 are amplified to the order of several volts. Potentiometer $R_1$ is provided for adjusting the gain at the output of amplifier 1.

The output of the amplifier is fed to filter 5 which removes 60 Hz and high and low frequency transients. Filter 5 is preferably a band pass filter with a pass band of ½ to 12Hz. The output of filter 5 is differentiated in differentiator 7, and the output of the differentiator is fed to sample and hold means 9. In one embodiment, the output of 9 is fed directly to multiplier 11.

A second output of amplifier 3 is fed to offset circuit 13 whose functions will be discussed below. One output of the offset circuit is fed to a second terminal of multiplier 11, while the other output of the offset circuit is fed to one input terminal of adder circuit 15 whose other input is fed from the output of the multiplier. The output of the adder is fed to both meter 17 and, in a feedback path, to another input of offset circuit 13. The meter is calibrated to read mm Hg.

In a preferred embodiment, a heater 10 is placed under the transducer to dilate the tissue under the transducer. The heater will dilate the tissue to near maximum dilation, and this is of utmost importance. However, if a heater is not provided, thermistor 19 can be supplied to contact the skin under the tissue. It is well known that activity of the sympathetic nervous system alters the calibre, and thus the volume, of the blood vessels in the microvasculature — except the capillaries. The change in calibre alters the fluid resistance and volume $V_i$. This causes changes in $$\frac{dV_t}{dt}$$

unrelated to changes in systolic pressure and consequently errors in indicated pressure.

Changes in the volume of the blood vessels of the skin produce changes in the rate of heat transfer from the blood, through the skin, to the air or surface in contact with the skin. The skin temperature thus depends on the rate of heat transfer across it and the temperature of the air in contact with it. For constant air temperature (room temperature ≃ 22°C), the skin temperature depends on its blood volume, increasing when the volume increases and vice versa.

Changes in skin temperature under transducer 1 can be used to compensate $$\frac{dV_t}{dt}$$

for errors in it due to slow changes in skin blood volume, caused by activity of the sympathetic nervous system.

The compensator 21 is merely an amplifier whose gain is adjusted by the output of the thermistor 19. The compensator and thermistor arrangements are used only when the heater 10 is not provided. However, the arrangement with the heater is preferred.

As was mentioned, it is possible to consider $T_c$ as either a constant or a variable, and the apparatus illustrated can monitor blood pressure under either assumption. Under most practical conditions, $T_c$ can be considered a constant, and under this assumption, both switches $S_1$ and $S_2$, which may be ganged, are set in position 1. With the switches in the 1 position, the output from 15 is effectively disconnected from the offset circuit, and the top of potentiometer $R_3$ is connected to a source of D.C. voltage. The output of 13 fed to the multiplier is effectively a 1 so that the multiplier circuit is, in effect, removed, and the output of either sample and hold 9 or temperature compensator 21 is fed directly to the input of adder 15.

Figure 2:
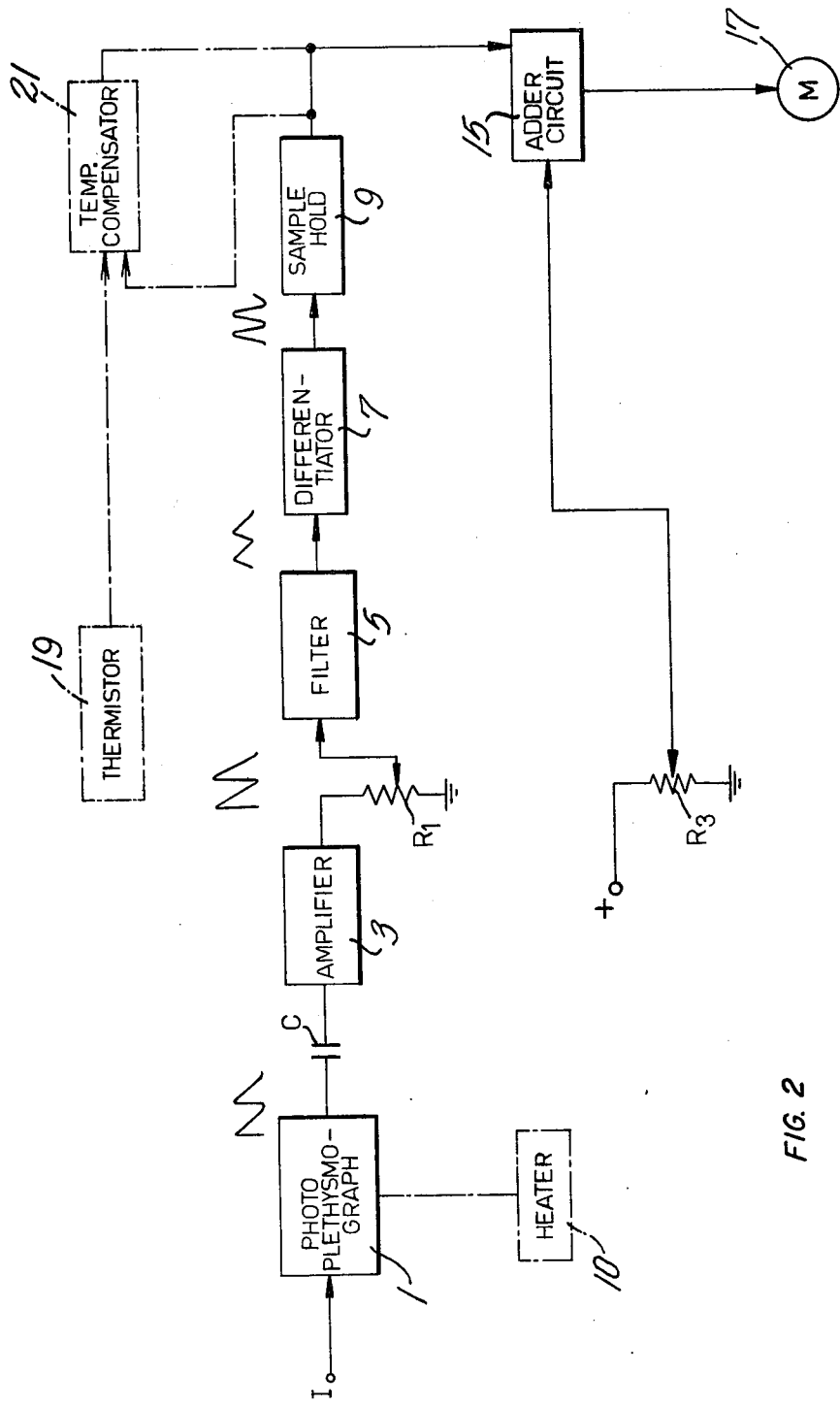
FIG. 2 is a block diagram of the apparatus wherein $T_c$ is considered a constant.

FIG. 2 illustrates the circuit arrangement with the switches in their 1 positions. As the assumption of a constant $T_C$ provides, for all practical purposes, accurate enough results, to a great extent the circuit of FIG. 2, without switches, constitutes a practical embodiment.

In considering the operation of the apparatus, we will first consider FIG. 2. Referring to FIG. 2, the output of 1 is a voltage which is proportional to the light intensity I, which is, in turn, proportional to the volume $V_i$ as discussed in the Appendices. This voltage is differentiated in 7 to provide a volatge proportional to $$\frac{dV_i}{dt}.$$

The constant of proportionality is set by adjustment of $R_1$ in a calibration procedure as will be discussed below.

In order to insure that samples are taken once every heart beat, sample and hold device 9 is set to sample at the beginning of diastole or at the maximin value of $$\frac{dV_i}{dt}$$

during diastole, in this case, when the derivative of the voltage, (output of 7) reaches its maximum value. The sample and hold device will hold a sampled value until it samples a new value.

The output of 9 is fed to one input of adder 15, whose other input is fed from the wiper arm of resistor $R_3$. $R_3$ is adjusted to correspond to the value of $P_2$ during a calibration procedure to be discussed below.

In order to calibrate the instrument, it is first turned on and allowed to warm up for a few minutes with the plethysmograph attached to the subject. Potentiometer $R_1$ is then turned to zero (the wiper arm is rotated so that it is adjacent to ground), and the diastolic pressure of the subject is measured with a sphygmomanometer and $R_3$ is adjusted until the meter reads ⅓ of the measured diastolic value, or some other suitable arbitrary value. With this adjustment, the insrument has been calibrated with a proper value for $P_2$. The circuit for following $$\frac{dV_i}{dt}$$

must now also be calibrated.

In order to effect the second calibration, the systolic pressure of the subject is taken, also with a sphygomomanometer, and $R_1$ is adjusted till meter M reads the measured systolic pressure. As can be seen, the constant of proportionality as between the conversion from volts to mm Hg, as well as the constant $K_5$, is provided by the adjustment of $R_1$.

With the instrument calibrated, and the tissue under the transducer heated, variations in light intensity, corresponding to variations in blood volume of tissue under the plethysmograph, are detected by the transducer and concerted to variations in the amplitude of an electrical signal, preferably a voltage. The voltage at the output of 1, of the order of milivolts, is amplified in amplifier 3 and raised to the order of several volts, and the output of the amplifier is fed to filter 5 in which a band of from ½ Hz to 12 Hz is passed.

The filtered signal is differentiated in differentiator 7, which could be, for example, an RC arrangement or other means well known in the art. The diastole portion at the output of the differentiator triggers the sample and hold means 9 so that a sample of the maximum value at the output of the differentiator during diastole is taken every heart beat of the subject, and the output of the sample and hold is fed, in the embodiment, where a heater 10 is not used, to the temperature compensator where it is modified in accordance with variations in the skin temperature of the subject.

The output of the compensator is, in turn, fed to the adder where a voltage representative of the steady pressure is added to it in the adder, and the output of the adder drives the meter 17 which is calibrated to translate the voltage at the output of the adder, representative of systolic pressure, to a reading in mm Hg.

As will be obvious, while pressure is being continuously monitored, readings will be provided at discreet intervals equal to the intervals between heart beats of the sbject. Means can be adapted to smooth these readings to provide a substantially continuous smooth curve.

Returning to FIG. 1, with switch $S_2$ set in its 2 position, the instrument is adapted to handle the situation wherein $T_c$ must be considered a variable. In this emobdiment, the time constant $T_c$ is derived from the rate of decay of the signal at the output of 3. the rate of decay is fed to one input of the offset circuit, and circuitry is provided at the input circuit to provide, at the No. 2 contact of the $S_2$ switch, a voltage representative of $T_c$. This voltage is then fed to multiplier 11 where it multiplies the voltage representative of $$\frac{dV_i}{dt}$$

so that a voltage representative of the second term on the right hand side of the first equation above is provided at the output of the multiplier.

The other input to the offset circuit is fed from the output of the adder circuit. This voltage is modified by a voltage representative of the voltage at the other input multiplied by e rised to the power $-(T/T_c)$ to produce a voltage representative of the first term on the right hand side of the first equation at the No. 2 position of switch $S_1$. The exponential is calculated in the offset circuit using a value T plugged into the offset circuit.

The first and second terms are added in the adding means 15 to provide a voltage representative of systolic pressure.

Except for the differences introduced by the offset circuit, as above described, the operation of the second embodiment is identical to the operation of the FIG. 2 embodiment.

As will be appreciated, the calibration procedure for the second embodiment is different and is as follows:

The instrument is turned on and allowed to warm up for a few minutes with the photoelectric plethysmograph attached to the subject. Next $R_1$ is rotated to zero and switch $S_1$ is set at position 1. In this position the 1 input to adder 15 is connected to the wiper of $R_3$. $R_3$ is again supplied with a fixed voltage. The diastolic pressure is measured with a sphygmomanometer, and $R_3$ adjusted to make Meter M read ⅓ the measured diastolic pressure, or other suitable value. Now the systolic pressure is measured and $R_1$ is adjusted to make Meter M indicate the measured systolic pressure. $S_1$ is next set to position 2 and control $R_4$ is adjusted to make Meter M indicate the measured systolic pressure again if it has changed. $R_4$ determines the value of $T^+$ in the computation of the voltage proportional to $$P_s \text{ EXP} \left[ -\frac{T^+}{T_c} \right].$$

The instrument is now calibrated and should follow changes in the systolic pressure.

Although the method and apparatus have assumed the sampling of the maximum value of the derivative during diastole, it will be clear that it would be possible to sample, instead, the maximum value of the derivative during systole to derive $$\frac{dV_t}{dt}.$$

In addition, although the disclosure mentions only a photoelectric plethysmograph, it is also possible to use an electrical impedance plethysmograph.

Although several embodiments have been described, this was for the purpose of illustrating, but not limiting, the invention. Various modifications, which will come readily to the mind of one skilled in the art, are within the scope of the application as defined in the appended claims.

APPENDIX A

Theoretical Model 4.1 Introduction

The circulatory system consists of a network of viscoelastic tubes through which blood is pumped by the heart. Like any other fluid dynamic system, it is characterized by pressure, flow, and resistance. The systolic pressure $P_s$ is one of the most important characteristic pressures in the system. The systolic pressure can be measured by various methods explained in Chapter III or it can be calculated from the mean pressure $P_m$ and the pulse pressure $P_p$. A new approach to follow changes in $P_s$ through measurement of a different variable is given.

4.2 Characteristic Pressures of the Circulatory System

The essential features of the circulatory system were explained in Chapter II. It was seen that at periodic intervals, the heart ejects a quantity of blood (stroke volume) into the circulation, raising its pressure. During ejection, some of it dilates the blood vessels; the rest flows directly through the microcirculation. After ejection ceases, i.e., during diastole, blood continues to flow in the circulation due to the elastic recoil of the arteries and is accompanied by a decrease in pressure.

A typical pressure-time relation in a major artery is shown in FIG. 4.1. The pressure alternates between 120 mm Hg (systolic) and 80 mm Hg (diastolic). The mean pressure is about 93 mm Hg. The exact mean pressure $P_m$ over a cycle is given by the area under the curve divided by the period of the cycle. That is, $$P_m = \frac{\int_{t_1}^{t_2} P_a(t) dt}{t_2 - t_1}$$

where
$P_m$ = mean arterial pressure in mm Hg.
$P_a(t)$ = instantaneous arterial pressure in mm Hg.
$t_1$ = beginning of heart cycle.
$t_2$ = end of heart cycle.

The mean pressure is usually averaged over several cycles for better accuracy. A good approximation to the mean pressure is found by the formula given by Catton [22] and is, $$P_m = \frac{P_s + 2P_d}{3} \tag{4.1}$$

where
$P_s$ = arterial systolic blood pressure in mm Hg
$P_d$ = arterial distolic blood pressure in mm Hg The pulse pressure $P_p$ is defined as the difference between the systolic and diastolic blood pressures in a cycle, i.e.

$$P_p = P_s - P_d \tag{4.2}$$

The simultaneous equations (4-1) and (4-2) may be solved to give, $$P_s = P_m + \tfrac{2}{3} P_p \tag{4.3a}$$
$$P_d = P_m - \tfrac{1}{3} P_p \tag{4.3b}$$

The non-oscillatory part of the arterial blood pressure is the weighted average $P_m$ of the systolic and diastolic pressures. The four pressures - systolic, diastolic, pulse, and mean-are the standard pressures used for characterizing the pressure aspects of the circulatory system.

4.3 New Pressure Relations 4.3.1 preliminary considerations

New pressure relations in the circulatory system can be used to give $P_s$ by writing the right-hand side of Equation (4.3a) differently. FIG. 2.2 is redrawn schematically to show the microcirculation more clearly, as in FIG. 4.2, for the period of diastole, i.e. when the aortic valve is closed. The pulmonary circulation is not shown as it is not relevant to this discussion. The regions $M_1, M_2, \ldots M_n$ are microvascular areas containing arterioles, metarterioles, capillaries, A-V anastamoses, and venules. Each is fed by a small artery and drained by a small vein. The instantaneous volume of blood in each region $M_1$, is $V_1$ where $i=1,2,3,\ldots n$. The blood flow through each region is $Q_i$ and is due to the elastic recoil of the arterial system. $P_c$ is the pressure in the large arteries referred not to a datum of zero but to a pressure $P_o$. That is, $$P_c = P_a - P_o \tag{4.4}$$

where
$P_a$ = arterial pressure in mm Hg
$P_o$ = reference pressure in mm Hg

In the discussion to follow, $P_a$ will be referred to as the pressure in the large arteries but is not to be taken as systolic pressure. $V_a$ is the volume of the large arteries at pressure $P_a$. $V_{ao}$ is the volume at zero pressure, i.e. $P_a = 0$.

4.3.2 Conditions and Assumptions

1. The model is chosen to be effective only at the beginning of diastole. At this time, the aortic valve is closed and all blood flow is due to the elastic recoil of the large arteries-mainly the aorta. The fall of pressure is monotonic and the pulsatile nature of the arterial blood pressure need not be considered.
2. The blood vessels of a particular microvascular region, $M_i$, are assumed to be maximally dilated and to remain so.
3. The blood viscosity in the microvascular region is assumed to be constant.
4. The blood is assumed to be incompressible.
5. Assumptions (2) and (3) above mean that the fluid resistance in the particular microvascular region $M_i$ is constant.
6. The pressure in the aorta at closure of the aortic valve is a constant fraction of the systolic pressure.
7. No pressure drop is assumed to occur in the aorta and large arteries. The pressure in the vena cavae and large veins is assumed to be zero.
8. A region $M_i$ is taken to include the part of the small artery feeding it and the part of the small vein draining it.
9. It is assumed that the pressure across the microvascular region $M_i$ is a constant fraction of the arterial pressure $P_a$. This is justified because it is assumed that no pressure drop occurs in the large arteries and that the small arteries in the vicinity of $M_i$ which feed it and the the small veins which drain it are maximally dilated.
10. The stiffness of the microvascular region $M_i$ is constant.
11. The walls of the aorta and large arteries are assumed to be elastic rather than viscoelastic.

4.4 Analysis for Pressure Relations
4.4.1 Variable Component of the Pressure In this section, the pressure $P_a$ in the large arteries is shown to be proportional to the rate at which the blood volume of a microvascular region changes plus a variable factor $P_o$ employing the conditions and assumption described in Section 4.3. A modified form of FIG. 4.2 is illustrated in FIG. 4.3. The aorta and large arteries are lumped and drawn as a balloon with volume $V_a$, to emphasize their distensibility. The left ventricle is not shown because it is not a functional part of the outflow circuit when the aortic valve is closed. $M_i$ is a particular microvascular region within the dashed rectangular area. It is divided into two parts: a resistance $R_i$ and a distensible volume $V_i$. M represents all the rest of the body's microvasculature lumped together. $R_i$ is the fluid resistance of $M_i$ and R is the fluid resistance of M. The part of the heart cycle considered is just after closure of the aortic valve and the instantaneous values of the variable quantities are taken at this time. Blood is being squeezed out of volume $V_a$ due to its elastic recoil and the pressure $P_a$ is falling. The pressure $P_i$ in volume $V_i$ is:

$$P_i = \frac{\Delta P_i}{\Delta V_i}(V_i - V_{io})$$
$$= E_i(V_i - V_{io}) \qquad (4.5)$$

where
$P_i$ = Pressure in volume $V_i$ in mm Hg
$E_i$ = Stiffness of volume $V_i$ in mm Hg/ml
$V_i$ = Volume of microvascular region $M_i$ in ml at pressure $P_i > 0$
$V_{io}$ = Volume of microvascular region $M_i$ in ml at pressure $P_i = 0$
= Constant
$\Delta P_i$ = Change of pressure $P_i$
$\Delta V_i$ = Change of volume $V_i$ due to $\Delta P_i$ since the pressure $P_i$ is proportional to $P_a$ by assumption $$P_i = k_i P_a = k_i (P_c + P_o) \qquad (4.6)$$

where
$k_i$ = Proportionality constant
substituting Equation (4.6) in Equation (4.5)

$$k_i(P_c + P_o) = E_i(V_i - V_{io})$$

or $$P_c = \frac{E_i}{k_i}(V_i - V_{io}) - P_o \qquad (4.7)$$

Since $P_c$ is decreasing, volume $(V_i - V_{io})$ must also be decreasing at the same rate since $$\frac{E_i}{k_i}$$

is a constant,
thus differentiating Equation (4.7)

$$\frac{dP_c}{dt} = \frac{E_i}{k_i} \cdot \frac{dV_i}{dt} \qquad (4.8)$$

The rate at which the volume of $V_a$ is decreasing is equal to the rate of outflow from it. That is, $$\frac{dV_a}{dt} = Q_{in} + Q_{i\ in} = Q_t \qquad (4.9)$$

where $\frac{dV_a}{dt}$ = volume rate of change of $V_a$ in ml/sec.

$Q_{in}$ = inflow to Region M in ml/sec.
$Q_{i\ in}$ = inflow to Region $M_i$ in ml/sec.
$Q_t = Q_{in} = Q_{i\ in}$
but also $$Q_t = \frac{P_a}{R_t} = P_a\left(\frac{1}{R} + \frac{1}{R_i}\right)$$

$$= \frac{P_a R R_i}{R + R_i} \qquad (4.10)$$

where
$R_t$ = Total fluid resistance
$R$ = Fluid resistance of M
$R_i$ = Fluid resistance of $M_i$
Substituting Equation (4.10) in Equation (4.9)

$$\frac{dV_a}{dt} = \frac{P_a}{R_t} = \frac{P_c}{R_t} + \frac{P_o}{R_t} \qquad (4.11)$$

The pressure $P_a$ in the distended volume $V_a$ is given by $$P_a = P_c + P_o = E_a (V_a - V_{ao}) \qquad (4.12)$$

where
$E_a$ = stiffness of volume $V_a$ in mm Hg/ml
$V_{ao}$ = volume of $V_a$ at reference pressure equals zero
= constant
Differentiating Equation (4.12) gives $$\frac{dP_c}{dt} = E_a \frac{dV_a}{dt} \qquad (4.13)$$

or $$\frac{dV_a}{dt} = \frac{1}{E_a} \frac{dP_c}{dt} \qquad (4.14)$$

Now substituting Equation (4.14) in Equation (4.11) and neglecting $P_o/R_t$. *

*$P_o/R_t$ is very small.

$$\frac{1}{E_a} \frac{dP_c}{dt} = \frac{P_c}{R_t}$$

or $$\frac{dP_c}{dt} = \frac{E_a P_c}{R_t} \qquad (4.15)$$

Finally substituting Equation (4.15) in Equation (4.8).

$$\frac{E_a P_c}{R_t} = \frac{E_i}{k_1} \frac{dV_i}{dt}$$

or $$P_c = \frac{E_i}{k_1} \frac{R_t}{E_a} \frac{dV_i}{dt} \qquad (4.16)$$

In this equation $E_i$ and $k_1$ are constants. The total fluid resistance $R_t$ and the stiffness $E_a$ are variables. They determine the rate at which $V_a$ and therefore $P_c$ decrease.

$$\frac{dV_i}{dt}$$

has its maximum value at the beginning of diastole and hence Equation (4.16) is only valid at the start of diastole. From Equations (4.4) and (4.16)

$$P_c = P_a - P_o = \frac{E_i}{k_1} \frac{R_t}{E_a} \frac{dV_i}{dt}$$

or $$P_a = P_o + \frac{E_i}{k_1} \frac{R_t}{E_a} \frac{dV_i}{dt} \qquad (4.17)$$

It was assumed in Subsection 4.3.2 that the arterial pressure at closure of the aortic valve is a constant fraction of the systolic pressure of the same cycle. Then $$P_o = k_2 P_s \qquad (4.18a)$$

where
$k_2$ = constant
Substituting Equation (4.18a) in Equation (4.17)

$$P_s = \frac{P_o}{k_2} + \frac{E_i}{k_1 k_2} \frac{R_t}{E_a} \frac{dV_i}{dt} \qquad (4.18b)$$

The significance of the datum or "steady" pressure $P_o$ will be discussed in the following subsection.

4.4.2 The Steady Component $P_o$

In the previous subsection, the pressure $P_c$ was defined as $(P_a - P_o)$. This pressure $P_c$ was shown in Equation (4.16) to be proportional to the time rate of change of a microvascular volume $V_i$ at the beginning of diastole and an expression for the arterial pressure $P_a$ was given in Equation (4.17). The origin and significance of pressure $P_o$ is explained in this subsection.

Consider Equation (4.15) without a restriction on the time interval and with the datum level equal to zero.

$$\frac{dP_a(t)}{dt} = \frac{E_a P_a(t)}{R_t} \qquad (4.15a)$$

solving for $P_a$ $$\int \frac{dP_a(t)}{P_a(t)} = \int \frac{E_a}{R_t} dt$$

$$\ln P_a(t) = \frac{E_a t}{R_t} + \ln P_a^*$$

$$P_a(t) = P_a^* \text{EXP} \left[ \frac{E_a}{R_t} t \right]$$

Since $P_a(t)$ is a decreasing function of time during diastole, the exponent of the exponential term is negative.

$$P_a(t) = P_a^* \text{EXP} \left[ -\frac{E_a}{R_t} t \right] \qquad (4.19)$$

where
$P_a^* = P_a\text{max.}$ = value of $P_a$ at $t = 0$ (i.e. beginning of diastole).

The fall of pressure in the large arteries is exponential and depends on the values of stiffness $E_a$ and the total peripheral resistance $R_t$. This is illustrated in FIG. 4.4a. A dog's femoral artery is occluded some time after systole and the pressure in the distal portion (away from the heart) is plotted versus time. The graphs are drawn for different hematocrit values. The hematocrit values are given in the top right corner of each graph. Only the solid-circle graphs are relevant to our discussion. The plots ought to be straight lines since the pressure scale is logarithmic. The plots show some curvature, particularly in the early parts of the graphs. This may be assigned to the fact that the stiffness $E_a$ is not constant but increases as the distending $P_a$ enlarges the artery[24].

This may be further explained by the relationship between aortic pressure and aortic volume which is shown in FIG. 4.5. Pressure is plotted versus the percentage increase of volume with reference to the volume at zero pressure. The measurements are made on 5 aortas removed from humans at autopsy. Five different age groups are represented. For the youngest age group, aged 20 to 24 years old, the curve is slightly sigmoid, but is fairly linear in the middle range. The stiffness ($\Delta P/\Delta V$) decreases slightly as the pressure increases from zero but increases again at high pressures.

In all of the other age groups, the stiffness increases as the pressure increases. At high intra-arterial pressures, $E_a$ will be larger and the time constant $R_t/E_a$ will be smaller, permitting a more rapid fall of pressure. As the pressure falls, $E_a$ diminishes, approaching a constant value at some lower pressure and the rate of fall of pressure also decreases. The blood viscosity rises as the hematocrit value increases, thus increasing the fluid resistance and reducing the rate of fall as shown in the figure.

The fall of pressure in the occluded dog femoral artery is shown more clearly in FIG. 4.4b. Here again, the femoral artery is occluded and the fall of pressure plotted against time. The pressure scale is logarithmic. The open circle curves are for pressure fall without drugs and the closed circle curve is for pressure fall after injection of 7.5 mg of Wyamine sulphate, which constricts the blood vessels. The rate of pressure fall after administration of Wyamine sulphate is clearly smaller than the rate before. After about 8 seconds both curves become reasonably straight, indicating that the time constants are no longer varying.

For the normal situation with no drugs (curves with open circles), in FIG. 4.4b, the pressure drop in the first 8 seconds is about 64 mm Hg. This gives an average rate of change of 64/8 or 8 mm Hg/sec. The fall of pressure in the next 27 seconds is about 7 mm Hg, giving an average rate of pressure drop of 0.26 mm Hg/sec. Since 0.26 is much smaller than 8.0, the average rate of change after 8 seconds can be taken as zero and the pressure at this time may be considered to vary very little from beat to beat. Then the pressure at the end of the initial 8-seconds period is:

$$P_o = P_a^* \, \text{EXP}\left[-\frac{E_a}{R_t} T^+\right] \quad (4.20)$$

where $T^+$ = value of $t$ in Equation (4.19) when $$\frac{dP_a(t)}{dt}$$

is very small.

= 8 seconds for above example.

The assumption of zero flow at a pressure $P_o$ is justified since in the dog flow is small at an arterial pressure of about 20 mm Hg. Therefore, the two pressures, $P_c$ and $P_o$, can be derived from FIG. 4.4b, using Equations (4.15) and (4.19).

From Equation (4.15) valid at start of diastole, $$\frac{dP_c}{dt} = \frac{E_a}{R_t} P_c$$

or $$P_c = \frac{R_t}{E_a} \frac{dP_c}{dt} = \frac{E_t}{k_1} \frac{R_t}{E_a} \frac{dV_t}{dt} \quad (4.21a)$$

From Equation (4.19) at $t = T^+$, $$\frac{dP_a}{dt} \simeq 0$$

and $$P_o = P_a^* \, \text{EXP}\left[-\frac{E_a}{R_t} T^+\right] \quad (4.21b)$$

$p_o$ is termed steady because it is not truly constant as Equation (4.21b) indicates where $P_a^*$ and $E_a/R_t$ are variables. However, $P_o$ is nearly constant. An increase in $P_a^*$ causes $E_a$ to become larger, and may be accompanied by a reduction of $R_t$. Some decrease in the time constant $R_t/E_a$ will take place, allowing the higher pressure to decay faster. This interaction between the various quantities tends to maintain $P_o$ constant in a particular individual.

4.5 Comparison Between the Standard and the New Pressure Relations

The relationship between $P_s$, $P_c$, $P_a$, and $P_o$ is shown in FIG. 4.6a. The systolic pressure is the sum of a variable component $P_c/k_2$ and a steady component $P_o/K_2$. If $E_a$ or $R_t$ changes, $P_o/k_2$ will take on a new value. However, the changes in $P_o$ will be small compared to those that can occur in $P_c$ from beat to beat.

In FIG. 4.6b, the relationships between the standard pressures $P_s$, $P_d$, $P_m$, and $P_p$ are shown. Here the systolic pressure $P_s$ is also the sum of a steady component $P_m$ and the variable part $P_p$. $P_m$ is seen to be greater than $P_o$ and reciprocally $P_p$ is less than $P_a$.

With a systolic pressure of 125 mm Hg and a diastolic pressure of 80 mm Hg, the mean pressure is:

$$P_m = \frac{P_s - 2P_d}{3} = \frac{125 - 160}{3}$$

$$= 95 \text{ mm Hg}.$$

In a normal male, to find $P_o$ one needs to know the values of $P_s$, $E_a$, $R_t$, and $T^+$. Let $T^+$ be 3 seconds, corresponding to a heart rate of 20 beats per minute. $E_a$ could be determined by referring to FIG. 4.5 and using Curve b. At a mean pressure of 95 mm Hg. the change in volume due to a 50 mm Hg pressure change is about 65 ml. This gives:

$$E_a = \frac{\Delta P}{\Delta V} = \frac{50 \text{ mm Hg}}{65 \text{ ml}} = 0.77 \text{ mm Hg/ml}$$

In Chapter II, the blood flow rate for a normal male was given as about 83 ml/sec. Then the total peripheral resistance $R_t$ is given by $$\frac{P_m}{Q_t} = \frac{95 \text{ mm Hg}}{83 \text{ ml/sec.}} = 1.14 \, PRU_s$$

For a systolic pressure of 125 mm Hg, $$P_o \simeq 125 \text{ EXP} \left[ \frac{-0.77 \times 3}{1.14} \right] \simeq 125 \times 0.135$$

$$\simeq 17 \text{ mm Hg.}$$

4.6 Diastolic Pressure

It should be possible to find the diastolic pressure $P_d$ from Equation (4.21b) by replacing the constant time interval $T^+$ with a variable time interval $T_d$, equal to the time interval between the start and end of diastole [2].

$$P_d \simeq P_a \text{ EXP} \left[ -\frac{E_a}{R_t} t_d \right] \quad (4.21c)$$

where $P_a = k_2 P_s$

Equation (4.22) can be checked for rough accuracy with data taken from the literature.

$E_a$ can be calculated from FIG. 4.5. Using Curve b, a change of pressure from 75 mm Hg to 125 mm Hg produces a percentage increase in volume of 85 percent at 75 mm Hg and 150 percent at 125 mm Hg. If the aortic volume at zero pressure is taken as 100 ml, [4]then the change in volume accompanying a pressure change from 75 mm Hg to 125 mm Hg is 250 ml − 185 ml = 65 ml.

The stiffness $$E_a = \frac{\Delta P}{\Delta V} = \frac{50}{65} = 0.77 \text{ ml/mm Hg.}$$

A table of pulse measurements taken from Neuman [35] is given in Table I. The measurements were taken on patients with renal hypertension. Consider the first subject No. 39. The subject's systolic pressure is 200 mm Hg and the diastolic pressure is 120 mm Hg. His mean pressure is:

$$P_m = \frac{P_s + 2P_d}{3} = \frac{200 + 240}{3} = \frac{440}{3} = 147 \text{ mm Hg.}$$

Assume that his cardiac output is normal—about 5 liters/min. or 83 ml/sec. Then the total peripheral resistance, $R_t$, is $$R_t = 147/83 = 1.77 \text{ PRU.}$$

Let the heart rate be normal, i.e. 72 beats/min. The period $T_p$ is 830 milliseconds. Then $t_d \simeq 0.6 T_p \simeq 500$ milliseconds. Let $K_2 = 0.8$, which is a reasonable value.

Finally $$P_d \simeq k_2 P_s \text{ EXP} \left[ -\frac{E_a}{R_t} t_d \right]$$

$$\simeq 0.8 \times 200 \times \text{EXP} \left[ -\frac{0.77}{1.77} \times 0.5 \right]$$

$$\simeq 160 \times \text{EXP} [-0.2175]$$

$$\simeq 160 \times 0.80$$

$$\simeq 128 \text{ mm Hg.}$$

The diastolic pressure for Subject No. 39 is 120 mm Hg. The calculated value of 128 mm Hg is only about 6.6 percent greater. This is a reasonably good agreement between measured and calculated values in accordance with elastic reservoir theory.

4.7 Summary

In this chapter a new set of relations have been derived to give the arterial systolic pressure $P_s$ under a number of conditions and assumptions. The expression for systolic pressure is derived as $$P_s = \frac{P_a}{k_2} \text{ EXP} \left[ -\frac{E_a}{R_t} T^+ \right] + \frac{E_i}{k_1 k_2} \frac{R_t}{E_a} \frac{dV_i}{dt} \quad (4.22)$$

where the quantities to be measured are $$\frac{dV_i}{dt} \text{ and } \frac{R_t}{E_a}.$$

If $R_t/E_a$ is considered constant (as it is in many situations), Equation (4.22) becomes $$P_s = P_1 + K_1 \frac{dV_i}{dt} \quad (4.23)$$

Where $K_1$ is a constant to be determined at calibration and $p_1$ has an almost constant value, since it is small compared to normal values of $P_c$.

The use of Equations (4.22) and (4.23) permits the estimation of the arterial systolic blood pressure from a single easily measurable primary variable—the change in microvascular volume $\Delta V_i$—after calibration against a standard systolic pressure measurement. The estimation is made with each heart beat so that continuous monitoring is possible.

APPENDIX B

TECHNIQUES OF MEASUREMENT

5.1 Introduction

In the previous chapter an expression (4.22) was derived to give the systolic pressure $P_s$ in terms of a number of constant and variable factors.

$$P_s = \frac{P_a}{k_2} \text{ EXP} \left[ -\frac{E_a}{R_t} T^+ \right] + \frac{E_i R_t}{E_a k_1 k_2} \frac{dV_i}{dt}$$

where $E_i$, $k_1$, $k_2$, and $T^+$ are constants and $$\frac{R_t}{E_a} \text{ and } \frac{dV_i}{dt}$$

are the variables to be measured.

Since $P_a = k_2 P_s$, $$P_s = P_s \text{ EXP} \left[ -\frac{T^+}{T_c} \right] + \frac{E_i R_t}{E_a k_1 k_2} \frac{dV_i}{dt} \quad (5.1)$$

$$= P_1 + K_1 T_c \frac{dV_i}{dt} \quad (5.2)$$

where $$T_c = \frac{R_t}{E_a} = \text{Time constant in seconds.}$$

$$K_1 = \frac{E_i}{k_1 k_2} = \text{Constant}$$

-continued $$P_1 = P_s \exp\left[-\frac{T^+}{T_c}\right]$$

$T_c$ and $$\frac{dV_t}{dt}$$

are now the two variables to be measured for obtaining $P_s$. Equation (5.2) can be used for following the changes in the systolic pressure $P_s$ by the following calibration procedure:
1. Determine the systolic pressure $P_s$ by standard means, such as auscultation.
2. Set $$P_s \exp\left[-\frac{T^+}{T_c}\right] = P_1$$

to an initial value using $P_s$ as determined above and an appropriate value of $T^+$.
3. Adjust $K_1$ in such a way as to make $$P_1 + K_1 T_c \frac{dV_t}{dt}$$

equal to $P_s$.
Now by updating the values of $T_c$ and $$\frac{dV_t}{dt}$$

in Equation (5.2) for each heart cycle, the changes in $P_s$ can be continuously followed. An electronic instrument may be developed to follow such changes in $P_s$ according to Equation (5.2). The only quantities to be measured are $$\frac{dV_t}{dt}$$

and $T_c$. In the following two sections, the techniques of measurement of these variables is explained.

5.2 Measurement of Rate of Change of Microvascular Volume $V_t$

There are a number of ways of measuring blood volume changes in a vascular bed [25]. Two methods, namely; electrical impedance plethylsmogrpahy and photoelectric plethysmorgraphy are discussed below.

5.2.1 Electrical Impedance Plethysmography

The electrical impedance plethysomgraph measures tissue impedance in various parts of the body. A schematic diagram of an impedance plethysmograph applied to an arm is shwon in FIG. 5.1. A high frequency constant current generator passes current from electrode No. 1 through the tissue of the arm to electrode No. 4. The frequency of the current usually lies between 20 and 100 kHz and its magnitude somewhere between 100 microamperes and 1 milliampere. The constant current produces a voltage across the tissue it traverses. This voltage is "tapped" off by electrodes No. 2 and No. 3 (receiving electrodes) which lead it to a detector-amplifier. The detectoramplifier produces an output signal which is proportional to the impedance of the tissue between electrodes No. 2 and No. 3.

Changes in tissue impedance between the receiving electrodes is taken to correpsond to changes in tissue blood volume [25]. The change in impedance produced by the blood volume pulse in the arm is illustrated in FIG. 5.2. The impedance varies between a minimum and a maximum with a waveform similar to that shown in FIG. 3.4. The rate of change of the blood volume is proportional to the time derivative of the impedance wave $Z(t)$.

$$\frac{dV_T(t)}{dt} \propto \frac{dZ(t)}{dt}$$

or $$\frac{dV_t}{dt} = C_1 \frac{dZ}{dt}$$

where
$Z(t)$ = Tissue impedance in ohms
$V_T(t)$ = Total volume of tissue in ml
$C_1$ = Proportionality constant
Since the changes in tissue impedance are caused by changes in tissue blood volume, this method can be used to find $$\frac{dV_t}{dt}.$$

However, it is useful only if the patient or subject, whose systolic pressure is being monitored, remains fairly motionless. Movement of the receiving electrodes relative to the skin will produce transient signals (artifacts). Almost any movement of tha arm will produce some electrode movement. This method is not suitable in any situation where the subject does not remain quiet.

5.2.2 Photoelectric Plethysmography

The photoelectric plethysmogrpah is another method used for indicating blood volume changes. This method is based on either on the absorption of light as it passes through body tissue and the blood flowing in it, or the reflection of light when it is incident on blood carrying tissue. Both these cases will be described below.

a. Absorption Photoelectric Plethysmography

The schematic of an absorption type plethysmograph is shown in FIG. 5.3a. A low power lamp operating on two or three volts passes light through a suitable portion of body tissue. Since some light must emerge from the tissue, the tissue cannot be too thick. Suitable body tissues are fingers, toes, pinna and lobe of the ear. In the figure, the light is shown passing through the ear lobe tissue. The emergent light falls on a photocell whose output is fed to an amplifier. The intensity of emergent light depends on the optical density of the tissue. Changes in optical density are taken to be proportional to changes in the amount of blood in the optical path. A plot of optical density versus time is shown in FIG. 5.3b. The optical density has a minimum and a maximum within each heart cycle. The waveform is similar to that of the impedance plethysmograph. The slope of the curve will give the rate at which the blood volume is changing. That is:

$$\frac{dV_T(t)}{dt} \alpha \frac{dD}{dt}$$

where
D = Optical density of tissue and blood
$V_T$ = Total volume of tissue and blood in optical path Actually, the transmitted light and its variations are detected by the photocell. Therefore, the optical density must be expressed in terms of light intensity. Or, more precisely, the rate of change of the absorption path is to be expressed as the rate of change of light intensity as shown next.

The transmission of light through an absorbing medium is governed by the Lambeurt-Beer Law [26].

$$I = I_o \, EXP \, [-\alpha C x] \quad (5.3)$$

where
I = Intensity of transmitted light
$I_o$ = Incident light
= Constant
$\alpha$ = Attenuation coefficient (light attenuation per unit concentration per unit length)
C = Amount of absorbent per unit volume
x = Length of absorbing path Taking natural logarithms of both sides of equation (5.3)

$$\ln I = \ln I_o - \alpha C x$$

or $$\ln(I/I_o) = -\alpha C x \quad (5.4)$$

The optical density of D is defined as $$D = -\text{Log}_{10}(I/I_o) = -0/434 \, \ln(I/I_o)$$

or $$\ln(I/I_o) = 2.304 \, \log_{10}(I/I_o) \quad (5.5)$$

Substituting Equation (5.5) in Equation (5.4)

$$2.304 \log_{10}(I/I_o) = -\alpha C x$$

$$\log_{10}(I/I_o) = -0.434 \, \alpha C x \quad (5.6)$$

or $$\log_{10} I = \log_{10} I_o - 0.434 \, \alpha C x \quad (5.7)$$

Differentiating $$\frac{d(\log_{10} I)}{dt} = -0.434 \, \alpha C \frac{dx}{dt} \quad (5.8)$$

This means that the time rate of change of the length of the absorbing medium is proportonal to the time rate of change of the logarithm of the intensity of the transmitted light. An expression for the rate change of the light intensity $$\frac{dI}{dt}$$

can be obtained directly by differentiating Equation (5.3).

$$\frac{dI}{dt} = -\alpha C \frac{dx}{dt} I_o \, EXP \, [-\alpha C x]$$

or $$\frac{dI}{dt} = -\alpha C \frac{dx}{dt} I \quad (5.9)$$

It will now be shown that in Equation (5.9), I can be considered constant.

Changes in transmitted light intensity are due to changes in the volume of tissue in the path of the light. these changes are due to variations in blood volume in the tissue. Measurements of the blood volume pulse in relation to total tissue volume have been done by Burch [27]. Tests carried out on twelve subjects showed a maximum blood volume pulse of 12.4 cu.mm. in 5 cc of tissue in fingers, toes and ears. The percent of volume change is 0.25. the mean volume pulse was 6.9 cu.mm. in 5 cc of tissue or 0.14 percent change.

The optical density of well dilated ear tissue is about 0.8 [28]. At this optical density the perecent change in light intensity I will be about 1.8 times the percent change in optical path length (tissue volume seen by transducer). Thus for a 0.25 percent change in tissue volume the transmitted light intensity will change by 0.46 percent. since this is less than 1.0 percent, I can be considered constant. Equation (5.9) can now be written as $$\frac{dI}{dt} = \alpha C I \frac{dx}{dt} \quad (5.10)$$

where
I = Constant

Changes in the linear dimensions x are assumed to be proportional to changes in tissue volume [29]. Since the photoelectric plethysmograph is used to detect changes in blood volume, this assumption is implicit in its use, Now $$\frac{dV_t}{dt}$$

can be substituted for $$\frac{dx}{dt}$$

in Equation (5.10) giving:

$$\frac{dI}{dt} = K_2 \frac{dV_t}{dt} \quad (5.11)$$

or $$\frac{dV_t}{dt} = K_3 \frac{dI}{dt} \quad (5.12)$$

where
$K_2, K_3$ = Constants b. Reflectance Photoelectric Plethysmograph

The schematic of a reflectance type plethysmograph is shown in FIG. 5.4a. In this case, the lamp and photocell are on the same side of the skin and can be placed almost anywhere on the body. Light from the lamp is reflected partly from the skin and partly from the vascular bed immediately beneath the skin. Some of the reflected light falls on the photocell producing a signal.

As in the case of the absorption type of photoelectric plethysmograph, the changes in reflected light intensity are taken to be proportional to blood volume changes. That is, $$\frac{dV_i}{dt} = K_4 \frac{di_r}{dt} \quad (5.13)$$

where $I_r$ = Reflected light intensity

The photoelectric plethysmograph is simple and inexpensive to use. Its electronic circuitry is less complex than that of the impedance plethysmograph. It is easy to apply the transducer to the body. Body movement produces artefacts in this case also but these are not as severe as those experienced with the impedance method. Therefore, the photoelectric plethysmograph is well suited to measure $$\frac{dV_i}{dt}.$$

5.3 Measurement of Time Constant of Large Arteries

The time Constant of the large arteries is:

$T_c = (R_t/E_a)$
From Equation (4.5)
$P_i^* = k_i P_a^* = E_i(V_i^* - V_{io}) = E_i \Delta V_i^* = E_i V_b^*$ where $V_i^*$ = maximum value of $V_i$ in a particular heart cycle.

$$P_a^* = \frac{E_i}{k_1} V_b^*$$

According to Equation (4.19)

$$P_a(t) = P_a^* \text{EXP}\left[-\frac{t}{T_c}\right]$$

substituting $$\frac{E_i}{k_1} V_b$$

for $P_a$ $$V_b(t) = V_b^* \text{EXP}\left[-\frac{t}{T_c}\right]$$

By measuring $V_b(t)$ at two instants $T_1$ and $T_2$, $T_c$ may be determined. Suppose $T_2 - T_1 = T_k$ = Constant; if starting time $T_1 = 0$
$T_k = T_2$
then $$V_b^* \text{EXP}[0] - V_b^* \text{EXP}\left[-\frac{t_2}{T_c}\right] = \Delta V_b^* \quad (5.14)$$

or $$V_b^*\left[1 - \text{EXP}\left[-\frac{t_2}{T_c}\right]\right] = \Delta V_b^*$$

$$-\text{EXP}\left[-\frac{t_2}{T_c}\right] = \frac{\Delta V_b^*}{V_b^*} - 1$$

Taking logarithms of both sides, $$\frac{t_2}{T_c} = \ln\left(\frac{\Delta V_b^*}{V_b^*} - 1\right) \quad (5.15)$$

or $$T_c = \frac{t_2}{\ln\left(\frac{\Delta V_b^*}{V_b^*} - 1\right)}$$

In order to measure time constant $T_c$ it is only necessary to measure $\Delta V_b^*$ and $V_b^*$ and make the calculation using a suitable value of $T_k$—say, 100 milliseconds.

In addition to being used in Equation (5.2), $T_c$ could be used as an indicator of the state of the arterial system.

5.4 Summary

In some situations, as when the subject is sitting or lying down, the arterial stiffness $E_a$ and total peripheral resistance $R_t$ vary very little. In these cases $T_c$ can be considered to be constant. Since $$P_z \text{EXP}\left[-\frac{T}{T_c}\right]$$

is of the order of 20 mm Hg, (Chap. IV, Subsection 4.4.2) an error of 20 percent in its value will cause an error of only about 3 percent when the systolic pressure is 125 mm Hg. If in addition the variations in $P_z$ do not exceed ± 25 percent, $$P_z \text{EXP}\left[-\frac{t}{T_c}\right]$$

can be considered constant, since an accuracy of ±5 percent is considered quite adequate for most blood pressure measurements.

Therefore, Equation (5.2) can now be written $$P_s = P_z + K_5 \frac{dV_i}{dt} \quad (5.16)$$

This leaves only one variable to be measured, $$\frac{dV_i}{dt},$$

and simplifies considerably the instrumentation.

In this chapter the techniques of measuring the variable quantities $$\frac{dV_i}{dt}$$

and $T_c$ have been discussed, thus laying the groundwork for the developement of appropriate instrumentation.

I claim:

1. A method for continuously monitoring systolic pressure in a human or animal subject by means of a calibrated instrument including light transducer means for converting variations in light intensity to variations in amplitude of an electrical quantity comprising:

detecting, with said transducer means, variations in light intensity corresponding to variations in blood volume of the tissue of said subject under said transducer means;

whereby the output of said tranducer means comprises variations in amplitude of said electrical quantity corresponding to said variations in blood volume;

differentiating said variations in amplitude of said electrical quantity with respect to time to provide a differentiated amplitude representative of the rate of said variations in blood volume;

periodically selecting a sample of said differentiated amplitude; and adding to said sample an amplitude of a like electrical quantity representative of a reference pressure;

to thereby produce an electrical signal whose amplitude is proportional to systolic pressure of said subject ; and providing said electrical signal to a display means to drive said display means whereby the magnitude of said systolic pressure is displayed on said display means.

2. A method as defined in claim 1 wherein said samples are selected once every heart beat of said subject.

3. A method as defined in claim 2 wherein said samples are selected at the beginning of diastole.

4. A method as defined in claim 3 wherein said amplitude of said reference pressure is a function of blood pressure in the aorta and large arteries of said subject, stiffness of said aorta and large arteries, and total peripheral resistance of the blood of said subject.

5. A method as defined in claim 4 and further comprising heating the tissue under the transducer means to dilate it to near maximum dilation.

6. A method as defined in claim 4 and further comprising monitoring skin temperature of said subject on the skin of said subject under said transducer means; and modifying said differentiated amplitude in accordance with variations in said skin temperature.

7. A method as defined in claim 4 where said electrical quantity is voltage, and wherein said instrument is calibrated to read in mm Hg.

8. A method as defined in claim 4 wherein said reference pressure is considered a constant, whereby said amplitude of said electrical quantity representative of said reference pressure is a constant amplitude;

including precalibrating the instrument comprising the steps of;

adjusting the instrument to read zero on the display means;

measuring the subject's diastolic pressure by some other means;

adjusting the amplitude representative of said reference pressure to read one third of said diastolic pressure, or other suitable value, on said display means;

measuring the subject's systolic pressure; and adjusting the sum of said sample and said amplitude representative of said reference pressure to read said systolic pressure on said display means.

9. A method as defined in claim 2 wherein said samples are selected at the maximum value of the differentiated signal during diastole.

10. A method as defined in claim 9 wherein said amplitude of said reference pressure is a function of blood pressure in the aorta and large arteries of said subject, stiffness of said aorta and large arteries, and total peripheral resistance of the blood of said subject.

11. A method as defined in claim 10 and further comprising heating the tissue under the transducer means to dilate it to near maximum dilation.

12. A method as defined in claim 10 and further comprising monitoring skin temperature of said subject on the skin of said subject under said transducer means; and modifying said differentiated amplitude in accordance with variations in said skin temperature.

13. A method as defined in claim 10 where said electrical quantity is voltage, and wherein said instrument is calibrated to read in mm Hg.

14. A method as defined in claim 10 wherein said reference pressure is considered a constant, whereby said amplitude of said electrical quantity representative of said reference pressure is a constant amplitude;

including precalibrating the instrument comprising the steps of;

adjusting the instrument to read zero on the display means;

measuring the subject's diastolic pressure by some othermeans;

adjusting the amplitude representative of said reference pressure to read one third of said diastolic pressure, or other suitable value, on said display means;

measuring the subject's systolic pressure; and adjusting the sum of said sample and said amplitude representative of said reference pressure to read said systolic pressure on said display means.

15. A calibrated instrument for continuously monitoring the systolic pressure of a human or animal subject comprising;

transducer means for detecting variations in light intensity corresponding to variations in blood volume of the tissue of said subject under said transducer means;

means for converting said variations in light intensity to variations in amplitude of an electrical quantity;

differentiating means for differentiating said variations in amplitude of said electrical quantity with respect to time to provide a differentiated amplitude representative of the rate of said variations in blood volume;

sampling means for periodically selecting a sample of said differentiated amplitude;

means for providing an amplitude of a like electrical quantity representative of a reference pressure;

adding means to add said sample and said amplitude representative of reference pressure;

whereby to produce an electrical signal whose amplitude is proportional to the systolic pressure of said subject; display means for receiving said electrical signal and displaying the magnitude of the systolic pressure.

16. An instrument as defined in claim 15 wherein said electrical quantity comprises a voltage and further comprising;
- voltage amplifier means for amplifying the voltage signal at the output of said converting means;
- said amplifier means comprising means for adjusting the gain thereof;
- and filter means for filtering the amplified voltage and for feeding said differentiating means;
- and wherein said means for providing a voltage amplitude representative of said reference pressure comprises a potentiometer and a source of voltage connected across said potentiometer, the output of said potentiometer being fed to said adding means.

17. An instrument as defined in claim 16 and further comprising compensating means for modifying said differentiated output in accordance with variations in temperature of the skin of the subject under said transducer means, said compensating means comprising an amplifier with variable gain;
- and thermistor means, adapted to be located on the skin of the subject under the transducer means, the output of said thermistor means being connected to said amplifier for adjusting the gain of said amplifier in accordance with said variations in skin temperature.

18. An instrument as defined in claim 16 and further comprising heating means for dilating the tissue under the transducer means.

* * * * *